US009414923B2

(12) United States Patent
Studer et al.

(10) Patent No.: US 9,414,923 B2
(45) Date of Patent: Aug. 16, 2016

(54) IMPLANT AND METHOD FOR PRODUCING AN IMPLANT

(75) Inventors: Armin Studer, Cham (CH); Jorge Garcia Forgas, Embrach (CH); Armando Salito, Wohlen (CH)

(73) Assignee: Warsaw Orthopedic, Inc., Warsaw, IN (US)

( * ) Notice: Subject to any disclaimer, the term of this patent is extended or adjusted under 35 U.S.C. 154(b) by 699 days.

(21) Appl. No.: 13/641,024

(22) PCT Filed: Apr. 12, 2011

(86) PCT No.: PCT/EP2011/055710
§ 371 (c)(1),
(2), (4) Date: Oct. 12, 2012

(87) PCT Pub. No.: WO2011/128334
PCT Pub. Date: Oct. 20, 2011

(65) Prior Publication Data
US 2013/0030544 A1    Jan. 31, 2013

(30) Foreign Application Priority Data
Apr. 15, 2010   (DE) .......................... 10 2010 010 599

(51) Int. Cl.
*A61F 2/32* (2006.01)
*A61F 2/36* (2006.01)
*A61F 2/30* (2006.01)
*A61F 2/28* (2006.01)
*A61F 2/40* (2006.01)

(52) U.S. Cl.
CPC ... *A61F 2/28* (2013.01); *A61F 2/30* (2013.01); *A61F 2/30767* (2013.01); *A61F 2002/30003* (2013.01); *A61F 2002/30004* (2013.01); *A61F 2002/3006* (2013.01); *A61F 2002/30011* (2013.01); *A61F 2002/30013* (2013.01); *A61F 2002/30028* (2013.01); *A61F 2002/30029* (2013.01); *A61F 2002/3092* (2013.01);
(Continued)

(58) Field of Classification Search
CPC ... A61F 2/28; A61F 2/30; A61F 2002/30003; A61F 2002/30004; A61F 2002/30013; A61F 2002/30011; A61F 2002/30028; A61F 2002/30029; A61F 2002/3006; A61F 2002/30321; A61F 2002/30767; A61F 2002/30906; A61F 2002/3092; A61F 2002/30929; A61F 2002/3093
See application file for complete search history.

(56) References Cited

U.S. PATENT DOCUMENTS 4,542,539 A * 9/1985 Rowe, Jr. ............ A61F 2/30767
606/76
6,645,248 B2   11/2003 Casutt
(Continued)

FOREIGN PATENT DOCUMENTS

EP    1647242 A1   4/2006
EP    2199423 A1   6/2010

*Primary Examiner* — Jacqueline Woznicki

(57) ABSTRACT

An implant is provided with a main body (1) and with a double coating applied to at least one surface section of the main body (1), wherein the double coating comprises an adhesion promoter layer (2), applied directly to the at least one surface section of the main body, and of an osteointegrative layer (3) covering the adhesion promoter layer (2). The layers (2;3) consist of pure titanium, wherein the adhesion promoter layer (2) has a thickness of 2-6 µm, in particular a thickness of 3-5 µm, and the osteointegrative layer (3) has a thickness of 50-70 µm, in particular of 55-65 µm. Moreover, the osteointegrative layer (3) has a porosity of 70-90% and a roughness $R_z$ of at least 45 µm. A related method is also provided for producing such an implant.

20 Claims, 2 Drawing Sheets

(52) U.S. Cl.
CPC . *A61F2002/3093* (2013.01); *A61F 2002/3097* (2013.01); *A61F 2002/3098* (2013.01); *A61F 2002/30321* (2013.01); *A61F 2002/30906* (2013.01); *A61F 2002/30929* (2013.01); *A61F 2002/30968* (2013.01); *A61F 2002/30971* (2013.01); *A61F 2310/00407* (2013.01)

(56) References Cited

U.S. PATENT DOCUMENTS

| | | | |
|---|---|---|---|
| 7,208,222 B2 * | 4/2007 | Rolfe et al. | 428/304.4 |
| 7,799,083 B2 | 9/2010 | Smith et al. | |
| 7,875,075 B2 | 1/2011 | Schwab | |
| 2003/0153981 A1 * | 8/2003 | Wang | A61F 2/30767 623/22.21 |
| 2006/0116774 A1 * | 6/2006 | Jones et al. | 623/22.32 |
| 2007/0178222 A1 | 8/2007 | Storey et al. | |
| 2007/0233248 A1 | 10/2007 | Schwab | |
| 2008/0071381 A1 * | 3/2008 | Buscher et al. | 623/18.11 |
| 2008/0161927 A1 | 7/2008 | Savage et al. | |
| 2008/0234828 A1 | 9/2008 | Wagner et al. | |
| 2009/0005870 A1 | 1/2009 | Hawkins et al. | |
| 2010/0070036 A1 * | 3/2010 | Implicito | A61F 2/4611 623/17.16 |
| 2010/0298939 A1 | 11/2010 | Delfosse et al. | |
| 2011/0190888 A1 | 8/2011 | Bertele et al. | |

* cited by examiner

IMPLANT AND METHOD FOR PRODUCING AN IMPLANT

RELATED APPLICATIONS

This application claims the benefit of International Application No. PCT/EP2011/055710 filed Apr. 12, 2011, now publication No. WO 2011/128334, which claims priority to German Patent Application No. DE 102010010599, filed Apr. 15, 2010. The contents of each of these priority applications are incorporated herein by reference, in their respective entireties.

TECHNICAL FIELD

The present disclosure generally relates to medical devices, systems and methods for the treatment of musculoskeletal disorders, and more particularly, to an implant having a main body and a double coating applied to at least one surface section of the main body. Furthermore, a method is provided for producing such an implant.

BACKGROUND

As is known, many implants, prostheses or endoprostheses are produced of polyether ether ketone (PEEK). Compared to metallic materials, this material has the advantage that the Elastic modulus of PEEK corresponds more to the Elastic modulus of cortical bones than metallic materials could ever achieve. Moreover, PEEK is permeable to X-rays, as a result of which the physician can observe bone integration of, for example, vertebral cages by means of corresponding radiograms during follow-up treatment. This would not be possible with a titanium cage.

However, for some time, implants and the like which are produced of PEEK have become subject to criticism. It could be observed that the human or animal bone does not completely adhere to the implant and grow into the implant, respectively. The bones rather form a seam on the surface of the PEEK material. In case that such a seam formation can be discovered on an X-ray image, this means that bone adhesion has not happened and that there is no sufficient stability regarding the inserted implant.

As a result of this, the implant either has to be removed and be replaced by a new one, or the implant has to be firmly fixed to the bone by means of other surgical methods. Another surgery is associated with additional stress, pain, and corresponding surgical risks for the patient.

Metallic material, particularly titanium, fulfills optimal conditions regarding growth into animal or human bone structures. It is proven that the bones adhere to the titanium, and, provided that the surface is accordingly designed, the bone can also grow into the microstructures of titanium materials.

Thus for a long time, there have been attempts to develop coatings and implant materials, respectively, such that, on the one hand, an improved bioactive surface layer and a related grow-into ability for animal or human bones is achieved, and, on the other hand, good Elastic moduli, as already realized through the usage of PEEK materials, can be obtained.

In EP 1372749 B1, a bioactive surface layer for implants and prostheses is disclosed, wherein the implant can consist of PEEK. A variable part of the surface layer consists of calcium phosphate phases, wherein the CA-ions and $PO_4$-ions embedded in the surface layer are completely spread over a metal oxide layer. The metal oxide is titanium oxide, for instance. Furthermore, an additional coating of the surface layer with hydroxylapatite is described. Such hydroxylapatite coatings of implants are common methods to ensure improved growth of bone structures into the implant.

However, tests of the tensile strength values to be achieved and of the shearing forces to be resisted of common implants have fueled the desire for improved implants regarding the two values, but wherein the implants should also grow into animal or human bone structures in such a good manner, as is the case with an implant coating with hydroxylapatite, for instance.

Due to the aforementioned, the task of the embodiments presented here therefore is to provide an improved implant and method, comprising a coating which can be realized cost-efficiently, has improved tensile strength values, and which can be loaded with higher shearing forces. Furthermore, a method is provided, with the help of which a quick and cost-efficient production of a coated implant can be realized.

SUMMARY

Brief Description of the Drawings

The present disclosure will become more readily apparent from the specific description accompanied by the following drawings, in which.

DETAILED DESCRIPTION

Figure 1:
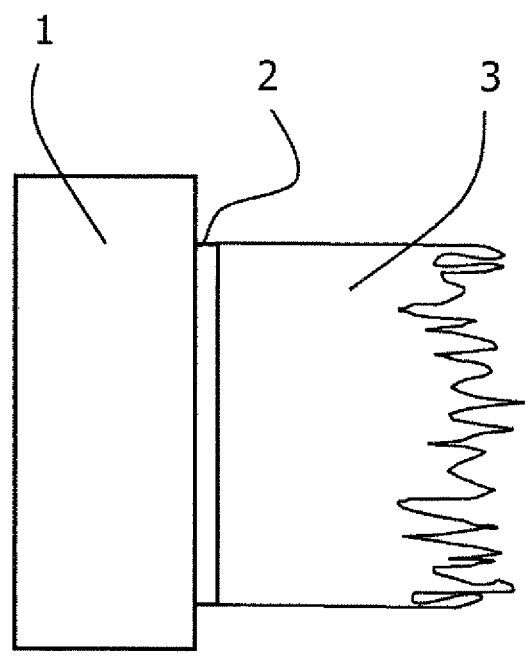
FIG. 1 shows a cross-sectional view through an implant according to one embodiment.

In one embodiment, an implant comprises a main body, wherein a double coating is partially applied to the surface of the main body. It is conceivable to apply the double coating to the entire surface of the implant main body, but due to cost and dimensioning reasons regarding the overall thickness of an implant, merely individual surface sections or only one surface section of the main body should be provided with said coating. Prior to the production method, the surface sections to be coated have to be calculated, namely depending on the implant to be produced and the size of the implant.

For instance, the implant can be vertebral cages, knee and hip prostheses and endoprostheses, respectively, bone prostheses or artificial shoulder joints. The implant embodiments herein are important particularly in matters of cementless prosthetics, but also in dental prosthetics.

When determining the surface sections, the size of the patient undergoing surgery is also important. For instance, implants, prostheses, and endoprostheses have different dimensions, depending on gender, size or weight of the patient. In case of implants for insertion in animal bodies, there are also often different implant sizes provided. The surface section(s) to be coated has to be dimensioned depending on the later load, tension, and the shearing forces applied to the implant in the inserted state. For instance, it can be sufficient in some cases, to determine a single continuous surface section, however, it is also conceivable to define several surface sections which are spaced apart from each other.

In the inserted state, i. e. when the implant is inserted in the human or animal body, the at least one surface section to be coated of the implant main body is directed to a bone of the body. With the double coating to be applied, the surface section(s) form the surface(s) of the implant adjacent to the bone.

First of all, said double coating consists of an interlayer and an adhesion promoter layer, respectively, which is directly applied to the determined surface sections and the determined surface section of the implant main body, respectively.

This adhesion promoter layer is completely covered with an osteointegrative layer. Both layers, i.e. the adhesion promoter layer and the osteointegrative layer, consist of pure titanium. For the adhesion promoter layer, a layer thickness of 2-6 μm, in particular a thickness of 3-5 μm, is aimed for. The osteointegrative layer comprises a layer thickness of 50-70 μm, in particular of 55-65 μm. Provided that several surface sections of the implant main body to be coated are determined, the sections separated from each other respectively have to be provided with the same layer thickness regarding the adhesion promoter layer and the osteointegrative layer.

According to one embodiment, the osteointegrative layer has a porosity of 70-90% and a roughness $R_z$ of at least 45 μm. I. e., the value of roughness $R_z$ amounts to at least 45 μm, but can be greater, e. g. 55 μm.

The main body of the implant preferably is produced of polyether ether ketone (PEEK), wherein the main body can also consist of other synthetic material, such as polyoxymethylene (POM), polyaryletherketone (PAEK), polyetherimide (PEI), polymethylpentene (PMP), polyethersulfone (PES), polysulfone (PSU), polymethyl methracylate (PMMA) or polyethylene terephthalate (PETP).

Due to the fact that, as described, the osteointegrative layer is produced of pure titanium and that, as experience has shown, implant coatings of a different material tend to chip or break off, for instance, it is the task of the adhesion promoter layer in accordance with one embodiment, to establish a stable connection between the osteointegrative layer and the implant main body. Particularly through the selected porosity of 70-90% regarding the osteointegrative layer, such a layer would, directly applied to the previously defined surface sections of the PEEK implant main body, not achieve a sufficient and permanent adhesion, respectively.

Due to the fact that the adhesion promoter layer also consists of pure titanium, adhesion of the osteointegrative layer to the adhesion promoter layer is implemented without problems. The adhesion promoter layer comprises a high density, to which the final porous layer—the osteointegrative layer— is applied.

The porous layer, also called porous coating, ensures excellent instant implant stability as well as an outstanding adhesion of the animal or human bone to the implant. Even after an already longer implantation time of several years, a symptom of tiring concerning the stability of the implant can be observed.

In a particularly preferred embodiment of the implant, the adhesion promoter layer comprises a thickness of substantially 3 μm, wherein substantially in this case means that deviations of ±0.5 μm are possible.

The osteointegrative layer preferably has a layer thickness of substantially 60 μm. With this layer thickness, deviations of ±3 μm lie within the scope of possibility.

With the mentioned layer thicknesses, particularly good results can be achieved regarding the tensile strength values and the possibly applied shearing forces.

Furthermore, it is pointed out that an osteointegrative layer having a porosity of 80%±5% is particularly preferred.

The method for producing an implant/a coated implant initially comprises the step of applying a mask to the implant main body. The mask comprises dimensions and recesses, such that the at least one calculated and defined surface section is exposed, and the not to be coated surface sections are covered with the mask. The mask provided with recesses is preferably produced of silicone.

Afterwards, an application of the at least one surface section to be coated with a blasting material is implemented. This means that the exposed and non-covered surface of the implant main body is applied, i. e. blasted with the blasting material.

The blasting material preferably is special fused alumina, which causes roughening of the surface section when applied to the PEEK main body. This process is implemented at a pressure of 1 to 3 bar, preferably at 2 bar.

The roughening causes an improved adhesion of the adhesion promoter layer applied to the at least one surface section of the implant main body in a subsequent step. The application of the adhesion promoter layer is implemented by means of a vacuum-based coating method, i. e. with a PVD method. In doing so, a layer having a thickness of 2-6 μm, in particular a thickness of 3-5 μm, of dense titanium material is applied to the surface section(s).

In another method step, this adhesion promoter layer or interlayer is provided with a final osteointegrative layer consisting of pure titanium. A layer having a thickness of 50-70 μm, in particular of 55-65 μm, is applied, which has a porosity of 70-90% and a roughness $R_z$ of at least 45 μm.

The porous coating, for instance, can be applied to the adhesion promoter layer by means of an electron melting method. In this case, sintering powder and titanium powder, respectively is applied layerwise to the adhesion promoter layer, and fused together and subsequently cooled according to the respective dimensions of the cross-sectional layer by means of energy application through a radiation source. The energy output by the radiation source only has an impact on the powder particles which are to be solidified, therefore representing a material particle of the later implant. Subsequently, the next cross-sectional layer is applied to the already fused material and is in turn melted by means of energy application. The process is implemented layer after layer in the vertical direction.

The electron melting method is particularly suitable to achieve the desired porosity of 70-90% of the osteointegrative layer.

The following results could be achieved with implemented tests of PEEK main bodies having a titanium double coating consisting of an adhesion promoter layer and an osteointegrative layer:

TABLE 1

| Tensile strength test according to ASTM F1044 | |
|---|---|
| | Tensile strength test according to ASTM F1147 |
| test run 1 (6 samples) | X = 59.7 MPa σ = 4.8 MPa |
| test run 2 (5 samples) | X = 56.4 MPa σ = 4.8 MPa |
| test run 3 (5 samples) | X = 35.6 MPa σ = 6.7 MPa |
| test run 4 (5 samples) | X = 41.5 MPa σ = 5.3 MPa |

TABLE 2

| Shearing force test according to ASTM F1044 | |
|---|---|
| | Shearing force test according to ASTM F1044 |
| test run 1 (5 samples) | X = 37.8 MPa σ = 1.7 MPa |
| test run 2 (5 samples) | X = 38.2 MPa σ = 4.3 MPa |
| test run 3 (5 samples) | X = 29.1 MPa σ = 2.8 MPa |

Hereafter, selected embodiments are explained in more detail with reference to the attached schematic drawings.

As shown in FIG. 1, an adhesion promoter layer 2 is applied to a main body 1 of the implant first of all. This adhesion promoter layer 2 is located on at least one surface section of the main body 1, wherein the number and the size of the surface sections are inter alia depending on the dimensions of the implants and the size, the weight, and the gender of the patient.

Prior to applying the adhesion promoter layer 2 to the surface section(s), the main body 1 is covered with a mask. This mask, for instance, consists of silicone and defines the surface section to be coated by means of recesses, i. e. the surface section is not covered by the silicon material of the mask.

Subsequently, the surface section is applied with a blasting material, preferably special fused alumina, at a pressure of 2 bar, in order to cause roughening of the surface section.

What follows is the coating of the roughened surface section with a very dense adhesion promoter layer 2 of pure titanium. This layer 2 comprises a thickness of 3 µm, wherein the application process is implemented by means of a PVD method.

In a final method step, the surface section provided with an adhesion promoter layer 2 is provided with an osteointegrative layer 3. This layer comprises a thickness of substantially 60 µm at a porosity of 80% and a roughness $R_z$ of 50 µm. The application of the osteointegrative layer 3 is implemented by means of an electron beam melting method on the basis of titanium powder.

Figure 2:
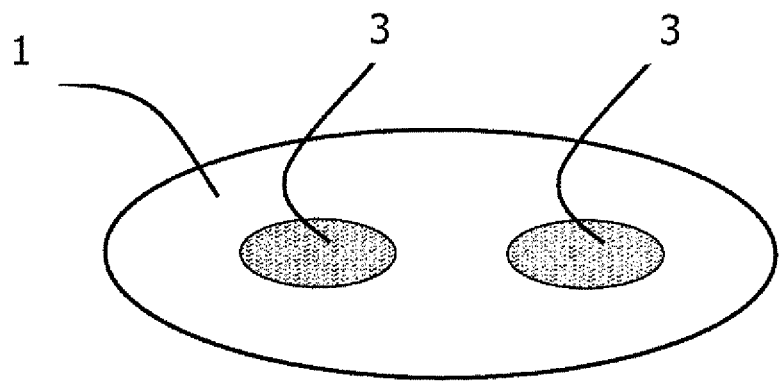
FIG. 2 shows a top view of a vertebral body implant according to one embodiment.

In FIG. 2, a vertebral body implant having a main body 1 is schematically illustrated. It is obtainable from the top view that two surface sections of the main body comprise a coating. Consequently, the osteointegrative layer 3 directed to the bone of the human or animal patient consists of two individual areas which are spaced apart from each other. The silicon mask used in the method for applying the double coating to the implant comprises two recesses in the form of both individual areas of the osteointegrative layer 3.

It should be noted that, when defining several surface sections of the main body, the layer thicknesses of the respective adhesion promoter layers 2 and osteointegrative layers 3 correspond, i. e. comprise substantially the same thickness values. However, deviations of ±0.5 µm do not play an important role.

The invention claimed is:

1. An implant having a main body including an outer surface having a roughened portion and a non-roughened portion that surrounds the roughened portion, the implant comprising a double coating applied to the roughened portion, wherein the double coating comprises:
   an adhesion promoter layer directly applied to the roughened portion; and
   an osteointegrative layer covering the adhesion promoter layer, the osteointegrative layer being adapted to contact a bone of an animal or a human body upon insertion of the implant into the animal or the human body,
   wherein the adhesion promoter and osteointegrative layers comprise pure titanium, the adhesion promoter layer comprises a thickness of 2-6 µm, the osteointegrative layer comprises a thickness of 50-70 µm, and the osteointegrative layer has a porosity of 70-90% and a roughness $R_z$ of at least 45 µm.

2. An implant according to claim 1, wherein the main body comprises polyether ether ketone (PEEK).

3. An implant according to claim 1, wherein the adhesion promoter layer comprises a thickness of 3 µm.

4. An implant according to claim 1, wherein the porosity of the osteointegrative layer is 80%.

5. An implant according to claim 1, wherein the adhesion promoter layer is completely covered by the osteointegrative layer.

6. An implant according to claim 1, wherein the adhesion promoter layer is denser than the osteointegrative layer.

7. An implant according to claim 1, wherein the main body comprises a material from a group consisting of polyoxymethylene (POM), polyaryletherketone (PAEK), polyetherimide (PEI), polymethylpentene (PMP), polyethersulfone (PES), polysulfone (PSU), polymethyl methracylate (PMMA) and polyethylene terephthalate (PETP).

8. An implant according to claim 1, wherein:
   the outer surface comprises a second roughened portion that is spaced apart from the roughened portion, the second roughened portion being surrounded by the non-roughened portion;
   a second double coating is applied to the second roughened portion such that the second double coating is spaced apart from the double coating, the second double coating comprising a second adhesion promoter layer directly applied to the second roughened portion and a second osteointegrative layer covering the second adhesion promoter layer; and
   the second adhesion promoter and second osteointegrative layers comprise pure titanium, the second adhesion promoter layer comprises a thickness of 2-6 µm, the second osteointegrative layer comprises a thickness of 50-70 µm, and the second osteointegrative layer has a porosity of 70-90% and a roughness $R_z$ of at least 45 µm.

9. An implant according to claim 1, wherein the adhesion promoter layer and the osteointegrative layer each consist of pure titanium.

10. An implant according to claim 1, wherein the double layer covers the roughened portion without covering any part of the non-roughened portion.

11. An implant, comprising:
   a main body including an outer surface having a roughened portion and a non-roughened portion that surrounds the roughened portion, the main body comprising a material selected from a group consisting of polyether ether ketone (PEEK), polyoxymethylene (POM), polyaryletherketone (PAEK), polyetherimide (PEI), polymethylpentene (PMP), polyethersulfone (PES), polysulfone (PSU), polymethyl methracylate (PMMA) and polyethylene terephthalate (PETP);
   an adhesion promoter layer having a bottom surface that directly engages the roughened portion; and
   an osteointegrative layer having a bottom surface that directly engages a top surface of the adhesion promoter layer, a top surface of the osteointegrative layer being adapted to contact a bone of an animal or a human body upon insertion of the implant into the animal or the human body,
   wherein the adhesion promoter and osteointegrative layers each comprise titanium, the adhesion promoter layer comprises a thickness that is less than that of osteointegrative layer and the osteointegrative layer has a porosity that is greater than that of the adhesion promoter layer.

12. An implant according to claim 11, wherein the thickness of the adhesion promoter layer is 2-6 µm and the thickness of the osteointegrative layer is 50-70 µm.

13. An implant according to claim 11, wherein the osteointegrative layer has a porosity of 70-90%.

14. An implant according to claim 11, wherein the osteointegrative layer has a roughness $R_z$ of at least 45 µm.

15. An implant according to claim 11, wherein the main body is a portion of a vertebral cage.

16. An implant according to claim 11, wherein the adhesion promoter layer is completely covered by the osteointegrative layer.

17. An implant according to claim 11, wherein the adhesion promoter and the osteointegrative layer each consist of pure titanium.

18. An implant according to claim 11, wherein:
- the outer surface comprises a second roughened portion that is spaced apart from the roughened portion, the second roughened portion being surrounded by the non-roughened portion;
- a second adhesion promoter layer directly applied to the second roughened portion such that the second adhesion promoter layer is spaced apart from the adhesion promoter layer; and
- a second osteointegrative layer covering the second adhesion promoter layer such that the second osteointegrative layer is spaced apart from the osteointegrative layer,
- wherein the second adhesion promoter and second osteointegrative layers comprise pure titanium, the second adhesion promoter layer comprises a thickness of 2-6 μm, the second osteointegrative layer comprises a thickness of 50-70 μm, and the second osteointegrative layer has a porosity of 70-90% and a roughness $R_z$ of at least 45 μm.

19. An implant according to claim 11, wherein the adhesion promoter layer covers the roughened portion without covering any part of the non-roughened portion.

20. An implant, comprising:
- a main body comprising opposite inner and outer surfaces, the outer surface having a roughened portion and a non-roughened portion that surrounds the roughened portion, the main body comprising polyether ether ketone (PEEK);
- an adhesion promoter layer having a bottom surface that directly engages the roughened portion, the adhesion promoter layer comprising a top surface opposite the bottom surface; and
- an osteointegrative layer having a bottom surface and an opposite top surface, the bottom surface of the osteointegrative layer being fused to the top surface of the adhesion promoter layer such that the osteointegrative layer completely covers the adhesion promoter layer, the top surface of the osteointegrative layer being adapted to contact a bone of an animal or a human body upon insertion of the implant into the animal or the human body,
- wherein the adhesion promoter and osteointegrative layers each consist of pure titanium, the adhesion promoter layer comprises a thickness of 2-6 μm defined by a distance between the top and bottom surfaces of the adhesion promoter layer, the osteointegrative layer comprises a thickness of 50-70 μm defined by a distance between the top and bottom surfaces of the osteointegrative layer, the osteointegrative layer has a density that is greater than that of the adhesion promoter layer, the osteointegrative layer has a porosity of 70-90%, and the osteointegrative layer has a roughness $R_z$ of at least 45 μm.

* * * * *